US012582992B2

(12) United States Patent
Alazzam et al.

(10) Patent No.: US 12,582,992 B2
(45) Date of Patent: Mar. 24, 2026

(54) METHODS AND DEVICES FOR RAPID DETECTION OF COVID-19 AND OTHER PATHOGENS

(71) Applicant: Khalifa University of Science and Technology, Abu Dhabi (AE)

(72) Inventors: Anas Alazzam, Abu Dhabi (AE); Habiba Alsafar, Abu Dhabi (AE); Waqas Waheed, Abu Dhabi (AE); Sueda Saylan, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 829 days.

(21) Appl. No.: 17/528,070

(22) Filed: Nov. 16, 2021

(65) Prior Publication Data

US 2022/0258167 A1 Aug. 18, 2022

Related U.S. Application Data

(60) Provisional application No. 63/124,218, filed on Dec. 11, 2020, provisional application No. 63/114,686, filed on Nov. 17, 2020.

(51) Int. Cl.
*B01L 7/00* (2006.01)
*C12Q 1/70* (2006.01)

(52) U.S. Cl.
CPC ................ *B01L 7/52* (2013.01); *C12Q 1/701* (2013.01); *B01L 2200/147* (2013.01); *B01L 2300/1827* (2013.01)

(58) Field of Classification Search
CPC ................ B01L 2300/1805; B01L 2300/1822
See application file for complete search history.

(56) References Cited

U.S. PATENT DOCUMENTS 4,865,986 A * 9/1989 Coy ........................ F25B 21/02
422/63
10,253,357 B2 4/2019 Mitra et al.
(Continued)

FOREIGN PATENT DOCUMENTS

CN 110272820 A 9/2019
JP H09322755 A 12/1997
(Continued)

OTHER PUBLICATIONS

"Extended European Search Report Received mailed on Mar. 21, 2023", for Application No. 21894149.0, 12 Pages.
(Continued)

*Primary Examiner* — Natalia Levkovich
(74) *Attorney, Agent, or Firm* — Billion & Armitage

(57) ABSTRACT

A device and method for detecting COVID-19 and other pathogens includes a sample compartment contained within an interior of the device and having multiple apertures for releasably receiving one or more test tubes containing a biological sample. A bottom portion of the test tube is contained within the interior of the device and a top portion of the test tube is exposed to atmosphere. The biological sample is lysed using the device; the lysed sample is mixed with one or more primers and then amplification (RT-LAMP) is performed using the device. A thermally conductive material on or in proximity to the sample compartment can facilitate precise heating of the compartment and sample. A thermally insulative material can be inside the interior of the housing. Multiple samples can be tested simultaneously. The results can be interpreted by a color change of the sample. The device is efficient, portable, reliable, and re-usable.

14 Claims, 12 Drawing Sheets

(56) References Cited

U.S. PATENT DOCUMENTS

| | | | |
|---|---|---|---|
| 2002/0006361 A1* | 1/2002 | Sanadi | B01L 3/5025 |
| | | | 356/246 |
| 2020/0224261 A1 | 7/2020 | Mann et al. | |

FOREIGN PATENT DOCUMENTS

| | | |
|---|---|---|
| KR | 20130090587 A | 8/2013 |
| KR | 20180023574 A | 3/2018 |
| WO | 2019153061 A1 | 8/2019 |
| WO | 2020016219 A1 | 1/2020 |

OTHER PUBLICATIONS

"Fact Sheet for Healthcare Providers", Lucira Health, Inc., Lucira Check-It COVID-19 Test Kit, Apr. 9, 2021, 3 pages.

"FDA Authorizes First Prescription At Home Molecular Test for COVID-19 Lucira Health test provides lab-quality result in 30 minutes or less from home", Nov. 18, 2020, 2 pages.

"Lucira Checkit COVID-19 Test Kit", Lucira Health, Obtained online on Feb. 15, 2022, 28 pages.

"Lucira COVID-19 All-In-One Test Kit", Lucira, Obtained online on Feb. 15, 2022., 6 pages.

Kaygusuz, Doijukan , et al., "DaimonDNA: A portable, low-cost loop-mediated isothermal amplification platform for naked-eye detection of genetically modified organisms in resource-limited settings", Sep. 15, 2019.

PCT/IB2021/060631 , "International Search Report and Written Opinion Received mailed Dec. 10, 2021", 12 pages.

Thompson, Dorian , et al., "Mini review: Recent progress in RT-LAMP enabled COVID-19 detection", Aug. 15, 2020, 32 pages.

\* cited by examiner

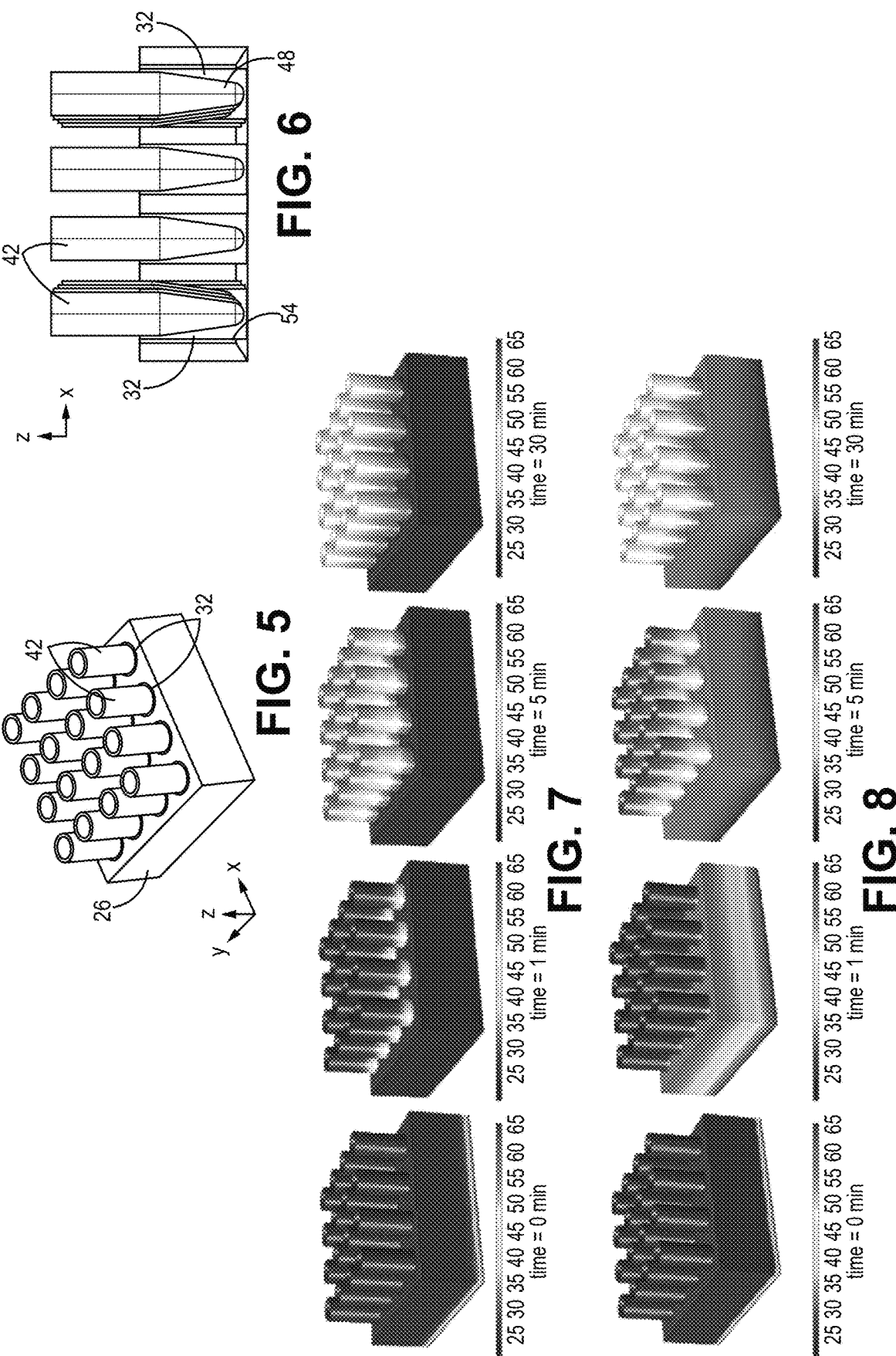

100

102 Collect swab sample

104 Lyse sample

106 Prepare lysed sample for amplification

108 Perform amplification reaction

110 Stop reaction and visually inspect

POSITIVE

OR

NEGATIVE

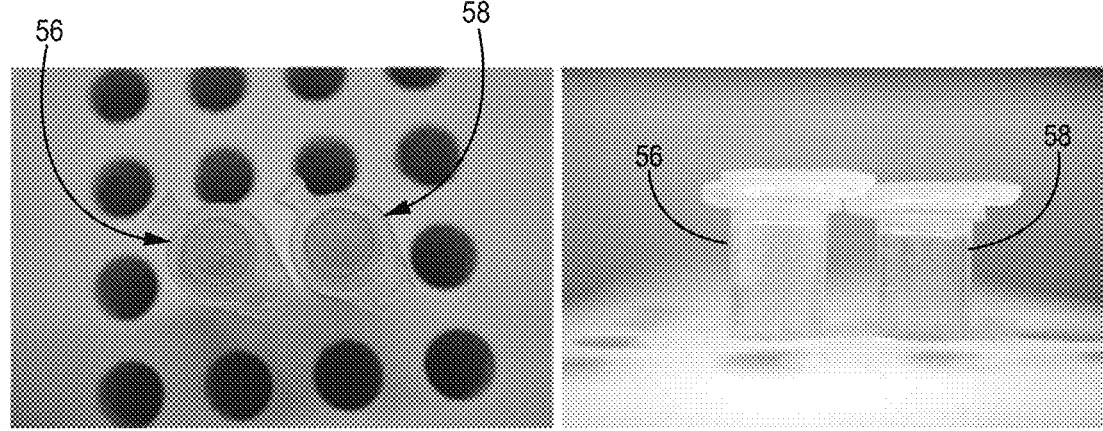
FIG. 13A          FIG. 13B

FIG. 14

COVID-19 Diagnostic Test through RT-PCR

(1) Nasopharyngeal swab <15 min

Cotton swab is inserted into nostril to absorb secretions.

(2) Collected specimen 0-72 h

Specimen is stored at 2-8°C for up to 72 hours or proceed to RNA extraction.

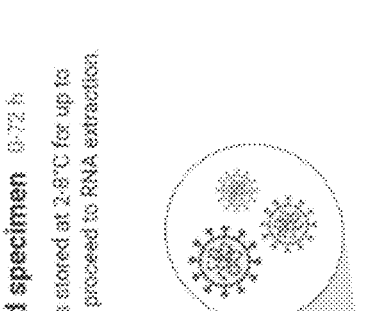

(3) RNA extraction ~45 min

Purified RNA is extracted from deactivated virus.

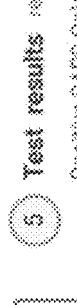

Deactivated virus

Purified RNA

(4) RT-qPCR ~2 h per primer set

Purified RNA is reverse transcribed to cDNA and amplified by qPCR.

Retro transcription

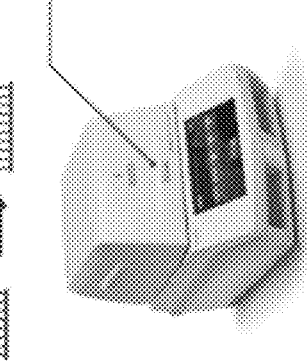

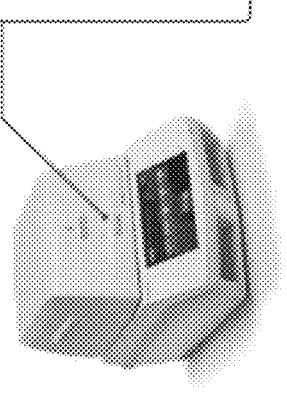

(5) Test results real-time

Positive SARS-CoV-2 patients cross the threshold line within 40.00 cycles (< 38.00 Ct).

Copies per reaction (Ct)

Fluorescence

Positive
Threshold
Negative

Cycle Threshold (C$_t$)

METHODS AND DEVICES FOR RAPID DETECTION OF COVID-19 AND OTHER PATHOGENS

CLAIM OF PRIORITY

This application claims the benefit of U.S. Provisional Application No. 63/114,686, filed on Nov. 17, 2020, and U.S. Provisional Application No. 63/124,218, filed on Dec. 11, 2020, the benefit of priority of which are claimed hereby, and which are incorporated by reference herein in their entirety.

BACKGROUND

In December 2019, a novel coronavirus emerged in Wuhan, China that was later dubbed as "sudden acute respiratory syndrome coronavirus-2" (SARS-CoV-2). The SARS-CoV-2 is responsible for causing an acute respiratory disease called the coronavirus disease 2019 (COVID-19 or COVID). After wreaking havoc in Wuhan, the disease rapidly spread across the globe within no time and was ultimately classified as a pandemic by the World Health Organization (WHO) on Mar. 11, 2020. The disease has impacted our daily lives in unprecedented ways and has put the whole world on a standstill inflicting heavy economical and emotional losses in addition to bringing illness, suffering, and death. According to the WHO, the number of positive cases by Mar. 8, 2021 has amounted to greater than 116.5 million people with more than 2.58 million fatalities. The major symptoms of COVID-19 are strikingly similar to previous respiratory diseases, such as SARS and MERS. Nevertheless, COVID-19, initially thought to damage only the lungs, exceeds beyond the lungs and affects other organs such as the heart, brain, kidneys, as well as the endocrine system. Moreover, COVID-19 is estimated to be far more contagious compared to influenza A, SARS, and MERS.

The COVID-19 pandemic has greatly strained the healthcare systems of many countries across the world, stretching them beyond their capabilities. This has forced many governments to declare a medical emergency and take unprecedented measures to ensure safety of their citizens. The global medical community is striving hard to contain the virus at the earliest, and the first step that emerges as part of the containment efforts is the rapid and accurate detection of SARS-CoV-2. The current molecular tests conducted in the labs and clinics are not enough to keep pace with the overwhelming number of cases emerging on a daily basis. Hence, there is an urgent need of introducing inexpensive and reliable diagnostic techniques/platforms that can be used in a point-of-care (POC) setting and aid in the screening of large masses away from the labs. These POC devices can reduce the number of unnecessary visits to the labs/hospitals and thus reduce the workload of healthcare staff, so that they can direct their endeavors towards critical patients. Additionally, reducing the number of clinical visits would reduce the risk of spreading the virus. Furthermore, the rapid POC-based molecular tests would enable the governments to conduct more diagnostic tests in parallel. Thus, more of the asymptomatic patients are likely to be detected, enabling a more efficient control in efforts to curb the spread of the pandemic.

Multiple methods are currently being employed by the medical practitioners to diagnose the COVID-19 disease. One of the most popular and accurate methods is the Real-Time Quantitative Polymerase Chain Reaction (RT-qPCR), which was declared by the WHO and the CDC as the "gold standard" for the detection of SARS-CoV-2. A molecular-based technique is an in-vitro nucleic acid amplification technique that is routinely used in the labs to turn small amounts of deoxyribonucleic acid (DNA) into large enough quantities so that it can be easily detected. For the SARS-CoV-2 detection, most of the current PCR systems/methods combine the reverse transcription step with the PCR (i.e., RT-qPCR) step to detect the RNA of the virus.

Unfortunately, the PCR method has limitations and is not free of problems. It is mostly difficult to perform the RT-qPCR process outside a specialized lab setting, as it requires some sophisticated equipment in combination with a highly-skilled workforce for successful operation. Moreover, it requires the sample to be heated (and cooled) to different temperatures for a specified amount of time in a single cycle; the cycle is then repeated multiple times to create a large number of copies of the target nucleic acids. Therefore, it necessitates a robust control and optimization of the heating/cooling modules operating at different temperatures, since their performance directly influences the PCR amplification efficiency. Any inconsistencies in the heating/cooling temperatures or transition times that may occur during the PCR cycles could result in non-specific or no amplification at all.

Detection of the amplification poses additional challenges. The traditional PCR systems make use of electrophoresis—a slightly slow method, requiring additional specialized equipment—for post-reaction detection. The real-time PCR (qPCR) systems are fast; however, the detection relies on bulky and sophisticated fluorescence-based equipment. These requirements not only add to the complexity of the PCR systems but also increase the cost and overall process time. Hence, it is currently quite challenging to utilize the PCR technique in the POC applications. Other detection methods—called serology tests—detect antibodies or antigens associated with SARS-CoV-2. The serology tests are rapid, easy to use, cheaper, less complicated, and allow POC operation. However, the antibody tests do not confirm the active state of infection in a patient, as they rely on the antibodies that the immune system of the patient produces in response to SARS-CoV-2. Moreover, these tests suffer from low accuracy, low sensitivity, and high false positive/negative results. Recently, biosensor-based detection has been introduced, but needs further investigation.

There is a need for and high demand to introduce a simple, inexpensive, portable, and rapid POC-based detection device and method for COVID-19, which is simultaneously sensitive and reliable.

SUMMARY

According to one or more aspects of the invention, a portable, reusable device for detection of one or more pathogens using a reverse transcription loop-mediated isothermal amplification (RT-LAMP) process can include a sample compartment contained within an interior of the device and having multiple apertures formed in a top surface, the multiple apertures aligned with exterior apertures formed on an exterior of the device, each of the apertures of the multiple apertures configured to releasably receive a bottom portion of a test tube containing a biological sample. A top portion of the test tube is exposed to atmosphere when the bottom portion is received in the aperture. The device can also include a heating source to increase a temperature of the sample compartment and the biological sample to a predetermined temperature when the test tube is received in the aperture, and a power source for providing electrical power to the heating source. Lysing and RT-LAMP can be separately performed on the biological sample using the device.

According to one or more aspects of the invention, a method of detecting one or more pathogens using a portable, reusable device can include providing the device for point-of-care testing. The device can comprise a housing formed by a plurality of interconnected walls and a sample compartment contained within an interior of the housing. The sample compartment can have multiple apertures formed in a top surface to align with exterior apertures formed in a top wall of the housing. The method can also include placing a bottom portion of one or more test tubes containing biological samples into the multiple apertures such that the bottom portion is contained in the interior of the housing and a top portion of the one or more test tubes is exposed to atmosphere, preheating the one or more test tubes to a predetermined temperature for a predetermined time to lyse the biological samples, transferring at least a portion of the lysed sample from the one or more test tubes into a second test tube and mixing the lysed sample with one or more primers in the second test tube to create a mixture, and performing reverse transcription loop-mediated isothermal amplification (RT-LAMP) on the mixture. The method can further include assessing a color of the mixture after the performing step to determine if the color is indicative of a negative or positive presence of the one or more pathogens, and repeating the steps above for new biological samples.

According to one or more yet further aspects of the invention, a reusable, compact device for detecting one or more pathogens using a reverse transcription loop-mediated isothermal amplification (RT-LAMP) process can include a sample compartment having a plurality of openings formed in a top side of the sample compartment, each opening configured to releasably receive a bottom portion of a container having a biological sample. The device can also include a heater attached to an underside of the sample compartment and configured to heat the sample compartment to raise a temperature of the biological sample to a predetermined temperature, a thermocouple configured to measure a temperature in the sample compartment, and a controller configured to regulate the heater based on the measured temperature. Lysing and RT-LAMP can be separately performed on the biological sample using the device.

This summary is intended to provide an overview of subject matter of the present disclosure. It is not intended to provide an exclusive or exhaustive explanation of the invention. The detailed description is included to provide further information about the present patent application.

BRIEF DESCRIPTION OF THE DRAWINGS

In the drawings, which are not necessarily, drawn to scale, like numerals may describe similar components in different views. The drawings illustrate generally, by way of example, but not by way of limitation, various embodiments discussed herein.

FIG. 5 is a perspective view of the sample compartment and test tubes, according to one or more embodiments of the present disclosure.

FIG. 6 is a cross-sectional view of the sample compartment and test tubes of FIG. 5, according to one or more embodiments of the present disclosure.

FIGS. 7 and 8 are schematics illustrating the temperature profiles for a heating simulation of the sample compartment and test tubes of FIGS. 3-6, according to one or more embodiments of the present disclosure.

FIGS. 13A and 13B are photographic images of two samples contained in test tubes to illustrate the impact of silicone oil in preparation of the samples, according to one or more embodiments of the present disclosure.

FIG. 14 is a schematic of a process (RT-PCR) used for diagnosing COVID-19.

DETAILED DESCRIPTION

Figure 1:
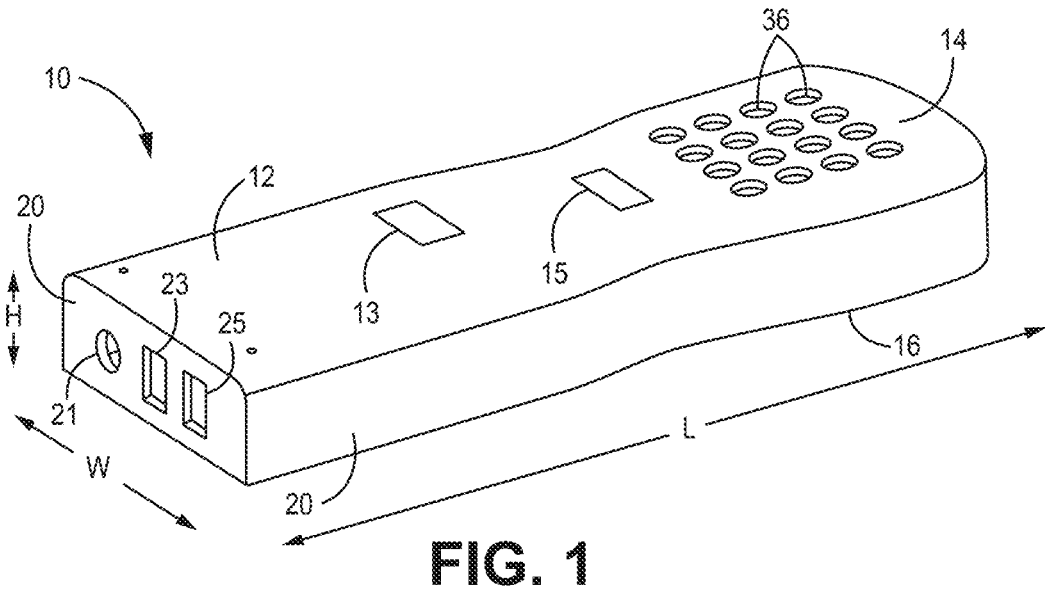
FIG. 1 is a perspective view of a rapid detection device, according to one or more embodiments of the present disclosure.

The present disclosure is directed to a portable, reusable device for rapid detection of one or more pathogens, including infectious agents, such as RNA virus, DNA virus (for example, herpes virus), and bacteria (for example, *Mycobacterium tuberculosis*). Examples of RNA viruses include, but are not limited to, SARS viruses (including SARS-CoV-2) and influenza viruses. The device uses reverse transcription loop-mediated isothermal amplification (RT-LAMP) on one or more biological samples to diagnose the one or more pathogens. Prior to performing RT-LAMP on the biological samples, the samples are lysed using the device. In the device and methods of the present disclosure lysing and RT-LAMP can be done using a single device and without the need for further testing or diagnostic equipment. The total processing time for both steps can be 45 minutes or less and multiple biological samples can be tested simultaneously. The results can be visually observed via a color change of the biological sample. The device can include a heating source and a low-voltage power source. After the biological samples are tested using the device, the samples can be disposed of, and the device can be used to perform testing on additional samples. The device can be used in a medical facility, at other institutions (private or public) including schools, or in a residential setting.

The RT-LAMP method is in a class of techniques referred to as "isothermal amplification", which appears to be a promising alternative to the PCR method. In contrast to PCR, the isothermal amplification techniques require only a single temperature to carry out the nucleic acid amplification. Furthermore, the temperature requirement in these techniques ranges typically from 37° C. to 65° C., much less than that used in the PCR denaturation step (~90° C.-95° C.). This greatly simplifies the heating requirements of the isothermal amplification-based systems as there is no need of thermocyclers anymore. In addition to LAMP, some of the examples include: helicase-dependent amplification (HDA), strand-displacement amplification (SDA), nucleic-acid sequence based amplification (NASBA), and rolling circle amplification (RCA).

A comparison of selective molecular and non-molecular for the diagnosis of COVID-19 is provided in Table 1 below.

Among the isothermal amplification-based diagnosis tests, LAMP has emerged as an attractive amplification method because of its simplicity, high tolerance against inhibitors, and its ability to amplify minimally processed or even raw samples. LAMP recognizes six to eight regions of the DNA and utilizes four to six primers, a strand-displacing DNA polymerase, and an additional reverse transcriptase in case of RNA amplification (i.e., RT-LAMP). The result is a highly specific, exponential amplification of the target nucleic acid in 20-60 minutes. This extensive synthesis facilitates the detection of the amplicon via a variety of techniques, which include the agarose-gel, real-time florescence detection using an intercalating DNA dye, turbidity, metal-sensitive indicator dye, or a pH-sensitive indicator dye in minimally buffered or non-buffered solutions. Moreover, for the latter, there is no need of specialized detection equipment since direct visual evaluation is possible. Among these detection techniques, the pH-sensitive dyes are regarded as the most favorable and convenient in allowing the LAMP to be used in a POC setting. A successful amplification produces hydrogen ions as a by-product, which changes the initially alkaline solution to an acidic

TABLE 1

| Selective Molecular and Non-Molecular Techniques for Detection of COVID-19 | | | | |
|---|---|---|---|---|
| | Molecular Test | | Anti-body Test | |
| | RT-PCR | RT-LAMP | ELISA | IgG/IgM Lateral Flow Assay | Antigen Test |
| What the test detects: | Viral RNA | Viral RNA | Antibodies | Antibodies | Viral Antigens (Specific proteins on surface of virus) |
| Sample taken from: | Nasopharyngeal Swab, sputum, saliva, stool | Same as RT-PCR | Blood | Human serum, plasma, or whole blood | Nasal or throat swab |
| Test setting: | Lab | Lab or Point-of-care | Lab | Point-of-care | Lab |
| Time required: | 3-4 h | Variable (35 min-3 h) | 1-3 h | 10-20 min | 15 min |
| Specificity: | High | High | High (after at least 14 days of active infection) | High (after at least 14 days of active infection) | Moderate |
| Sensitivity: | High | High | High (after at least 14 days of active infection) | High (after at least 14 days of active infection) | Moderate |
| What the test relays: | Active coronavirus infection | Active coronavirus infection | Past coronavirus infection | Past coronavirus infection | Active coronavirus infection |
| Pros: | Commonly used; gold standard | Rapid; results can be detected by naked eye | Simple and inexpensive | Simple; inexpensive; fast; visual inspection possible | Positive results are usually highly accurate |
| Cons: | Requires bulky, expensive, and specialized equipment to analyze the results; the time needed to complete the test is high; trained personnel is required. | The design of primers can be complex; more chances of primer-to-primer interaction; qualitative test (difficult to quantify the results (level of viral infection); chances of false positives because of spurious amplification | Not well established; it can take several days (even weeks) to develop antibodies up to a detectable level | A higher chance of missing an active infection (less sensitive than molecular tests); negative results may need to be confirmed via a molecular test. | A higher chance of missing an active infection (less sensitive than molecular tests); negative results may need to be confirmed via a molecular test. |
| Cost: | High | Moderate | Low | Low | Low | solution and reduces the pH value (by ≥2 pH units). This drop in the pH value is detected by a change in the color of a pH-sensitive dye that is added with other reagents.

In the device and methods of the present disclosure, RNA extraction does not have to be performed separately, which can be a time-consuming step for RT-LAMP and in some cases, requires additional instruments or equipment. As described further below, the device and methods disclosed herein include lysing the biological sample using the device and then performing amplification of the lysed sample with the same device.

Figure 2:
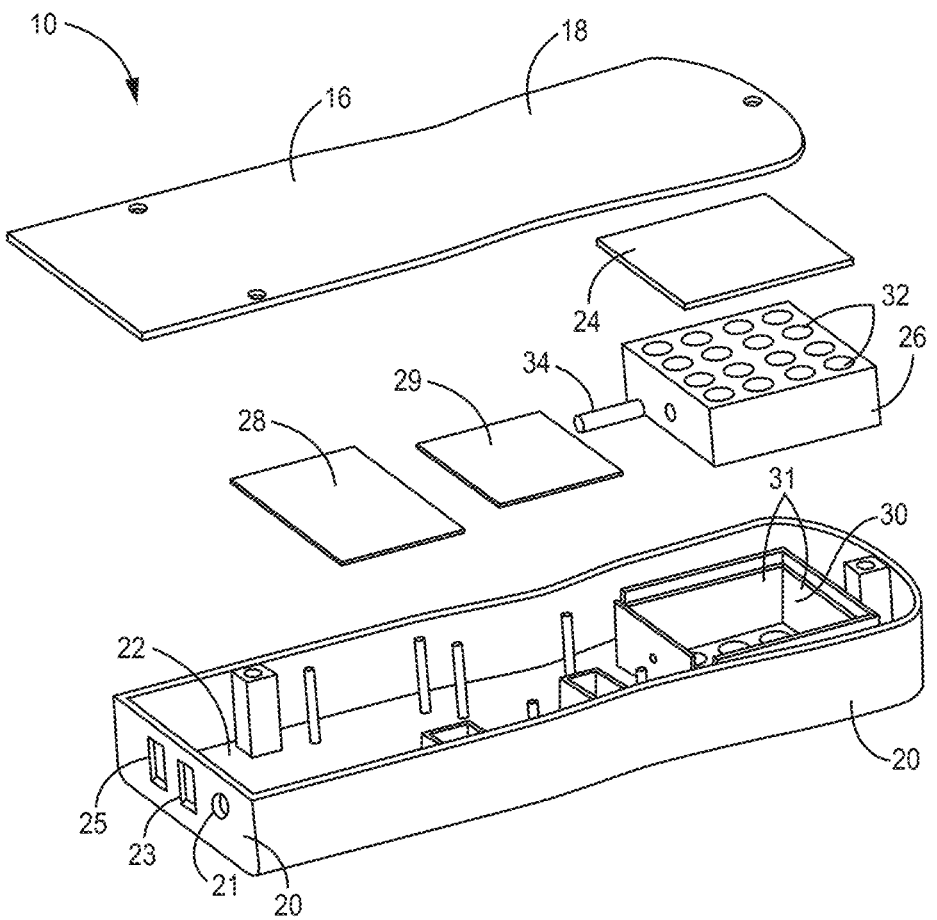
FIG. 2 is an exploded view of the device of FIG. 1 rotated 180 degrees, according to one or more embodiments of the present disclosure.

FIG. 1 shows an example of a device 10 for the detection of one or more pathogens, including SARS-CoV-2. FIG. 2 shows an exploded view of the device 10 (i.e., the device 10 in a disassembled position). An exterior 12 of the device 10 includes a top side 14 and a bottom side 16. The bottom side 16 can be formed by a removable cover 18. The exterior 12 includes side walls 20 to connect the top and bottom sides, 14, 16, respectively. The exterior 12 forms a housing for various components of the device 10. Power is supplied to the device 10 using an external 5 V AC-DC adapter (not shown in FIG. 1 or 2) that can be attached via a power connector 21.

The device 10 is designed for ease of use and portability and thus is intended to be small or compact. In an example, a height H of the device 10 is about 26 mm (about 1 inch), a width W is about 79 mm (about 3 inches) and a length L is about 205 mm (about 8 inches). It is recognized that the dimensions H, W and L can vary and may be smaller or larger than the example provided. An overall size of the device 10 may depend, in part, on how many samples the device 10 is capable of testing simultaneously or the intended user of the device (for example, point of care testing in a medical facility or in-home use).

In an example, one or more parts of the exterior 12 (housing) can be formed via three-dimensional (3D) printing. In other examples, one or more parts of the exterior 12 can be formed by injection molding or other fabrication technologies. The device 10 was designed using Creo Parametric 6.0.3.0 software.

The top side 14 of the exterior 12 can include digital displays 13 and 15 for relaying measured parameters, such as for example, time and temperature. An opening 23 can receive an on/off switch for powering the device 10 on and off. An opening 25 can receive a timer switch for resetting one or more timers for the device 10.

An interior 22 of the device 10 includes a heater 24, a sample compartment 26, a first control board 28 and a second control board 29. The sample compartment 26 can be received within a compartment housing 30 formed by rectangular walls 31 in the interior 22. This is one example of how the compartment 26 can be contained within the interior 22. The sample compartment 26 can include a plurality of apertures or openings 32 formed through a top of the sample compartment, each aperture or opening 32 configured to receive a portion of a test tube, or similar small-scale container, containing a biological sample or a control sample. The heater 24 can be a panel located between the sample compartment 26 and the bottom side 16. As described further below, the heater 24 can be used to maintain the samples at a predetermined temperature. The sample compartment 26 can include a thermocouple 34 that can be embedded inside the sample compartment 26 to measure the temperature in an interior of the compartment 26. In an example, the thermocouple 34 can be J or K type thermocouple.

The first and second control boards 28 and 29 can be printed circuit boards (PCBs) for monitoring and controlling one or more parameters during operation of the device 10. For example, control board 28 can be a timer control unit and control board 29 can be a temperature control unit. The outputs from the boards 28 and 29 can be relayed on the digital displays 13 and 15. In an example, the boards 28 and 29 can require 12V power, rather than 5V, in which case a DC regulator is included in the design of the device 10.

In the example shown in FIGS. 1 and 2, the device 10 is configured as a handheld portable device that can operate at a low voltage. In an example, the external power source can be a 5-volt adapter. The design of device 10 is highly scalable; for example, a larger size device 10 can have a larger heating module for the heater 24 and more electrical power. Although COVID is focused on herein as the specific pathogen being detected, the device 10 and methods herein are not limited to the detection of SARS-CoV-2. Other example viruses include, but are not limited to, influenza viruses and herpes viruses. The reagents that are used can be selected based on the specific pathogen. The timers and temperature controllers of the device 10 can be easily reprogrammed depending on the specific pathogen to be detected, without requiring a change in terms of electrical power or other parameters.

In an example, the apertures or openings 32 formed in the compartment 26 are cylindrical in shape. As described further below, a bottom portion of the test tubes or sample container can have a conical shape. As such, there can be some space between the conical portion of the tube and the cylindrical aperture 32. In an example, a thermally conductive material can be added to the apertures 32, before or after the tubes are placed in the apertures 32, to fill such space. This is described further below in reference to FIGS. 3 and 4. In another example, the sample compartment 26 can be fabricated such that a portion of the apertures 32 have a conical shape conforming to the bottom shape of the test tubes or container.

In the example of FIGS. 1 and 2, the sample compartment 26 includes sixteen apertures 32 and the apertures 32 are arranged in four rows of four apertures (four by four). In another example, the sixteen apertures shown in FIG. 2 can be arranged in other configurations—for example, two by eight, rather than four by four. In another example, more or less apertures 32 can be included in the sample compartment 26. The number and arrangement of the apertures 32 can depend on, for example, a size of the device 10 or the intended user. The design in FIGS. 1 and 2 with sixteen apertures 32 facilitates simultaneous testing of fourteen biological samples, a positive control and a negative control.

A plurality of apertures 36 are formed in the top side 14 of the device 10. When the sample compartment 26 is in the compartment housing 30, the apertures 36 align with the apertures 32 of the sample compartment 26 such that the test tubes can be inserted through the apertures 36 for temporary placement in the apertures 32. Thus, the number and arrangement of the apertures 32 corresponds to that of the apertures 36.

The RT-LAMP process is a nucleic acid amplification method to multiply specific sequences of RNA and diagnose infectious diseases that are caused by RNA viruses. During the RT-LAMP process, a temperature of the samples is kept generally constant given the temperature dependent activation of the reaction and the role temperature plays in specificity of nucleic acid amplification techniques. Thus, the device 10 has an efficient thermal design, including thermal isolation of components of the device 10 from other components.

Figure 3:
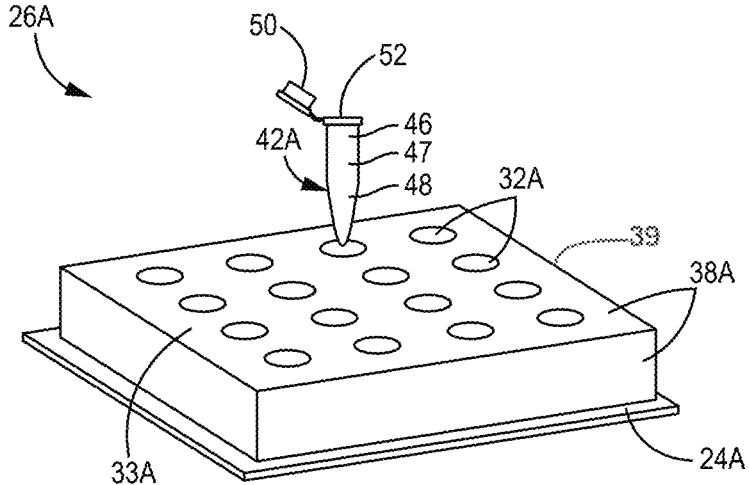
FIG. 3 is a perspective view of the sample compartment and heater of the device of FIG. 1, according to one or more embodiments of the present disclosure.
Figure 4:
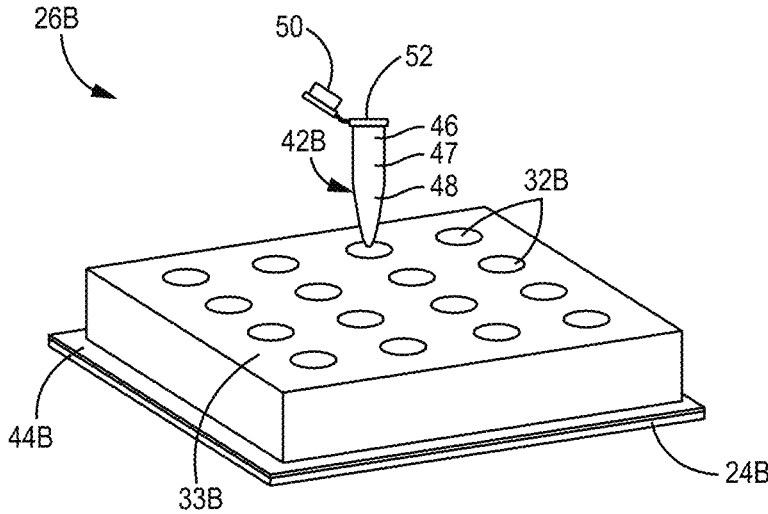
FIG. 4 is a perspective view of another example sample compartment and heater of the device of FIG. 1, according to one or more embodiments of the present disclosure.

FIGS. 3 and 4 provide examples of two designs of the sample compartment 26; both designs were evaluated for thermal control as described below in reference to FIGS. 5-8.

FIG. 3 illustrates a sample compartment 26A that includes a liner 38A and a plurality of apertures 32A formed through a top surface 33A of the sample compartment 26A. A test tube 42A is shown being inserted into one of apertures 32A. The liner 38A covers an exterior 39 of the sample compartment 26A. Excluding the liner 38A, the sample compartment 26A can be formed of a metal, such as aluminum. The sample compartment 26A can be solid, except for the apertures 32A formed in the compartment 26A. The liner 38A can be a thermally conductive material, such as, for example, an elastomer. In an example, the thermally conductive material is DOWSIL™ 3-6655 from Dow. To enhance thermal connection to the sample in test tube 42A, the liner 38A can provide thermal conduction of the compartment 26A. The heater 24A is shown below the sample compartment 26A for heating the compartment 26A and thus the biological sample or control sample within the test tube 42A. The liner 38A can be used to improve attachment of the heater 24A (physically and thermally) to the compartment 26A and the liner 38A can be added to the compartment 26A prior to attachment of the heater 24A. The liner 38A can be thin, for example having a thickness of between about 1 mm and about 10 mm. In another example, the thickness of the liner 38A can be between about 2 and 5 mm.

The liner 38A can also cover the exterior of the apertures 32A. By applying the liner 38A over the apertures 32A, the liner 38A can provide thermal conduction to the apertures 32A and adjust a shape of the apertures 32A to correspond more to a conical shape of the test tubes that are to be received therein. The material that forms the liner 38A can be casted or poured into the apertures 32A and then cured, for example, by heating at 65° C. for about 30 minutes. Such curing/heating step can be performed prior to testing samples in the device 10. In an example, the tubes can be placed inside the apertures 32A prior to curing. In another example, the heating step (for curing) is excluded and over time the liner material cures inside the apertures 32A.

FIG. 4 illustrates a sample compartment 26B, which is formed from a metal and excludes a liner over the metal. The sample compartment 26B includes a plurality of apertures 32B (formed through a top surface 33B) and a test tube 42B is shown being inserted into one of apertures 32B. The relationship between the tube 42B and the apertures 32B is similar to that described above in reference to FIG. 3. The notable difference in the design of FIG. 4 is a conductive layer 44B is used instead of the liner 38A of FIG. 3. The conductive layer 44B is located underneath an underside of the sample compartment 26B, between the sample compartment 26B and the heater 24B. The conductive layer 44B can provide a thermal connection between the heater 24B and the sample compartment 26B. The conductive layer 44B can be formed of a thermally conductive material, such as an elastomer. In an example, the conductive layer 44B is DOWSIL™ 3-6655 from Dow. The conductive layer 44B is used to connect the heater 24B to the compartment 26B. In an example, a thickness of the layer 44B can range from about 0.25 mm to about 10 mm, and in another example, from about 0.5 mm to about 5 mm. As described above in reference to the sample compartment 26A, a thermally conductive material can also fill a gap inside apertures 32B, and in an example, can be filled in a similar manner to described above for apertures 32A.

As demonstrated by the designs in FIGS. 3 and 4, the thermally conductive material can be located on or in proximity to the sample compartment 26A, 26B. The thermally conductive material can also be located on or in proximity to the surface of the apertures 32A, 32B.

The test tube 42A, 42B includes a top portion 46 and a bottom portion 48. The top portion 46 include a cap 50 and a ring 52 configured to releasably seal the cap 46. A middle portion 47 separates the top portion 46 from the bottom portion 48. The bottom portion 48 has a conical shape and is configured to be temporarily secured inside the apertures 32A, 32B. The design of the sample compartment 26A, 26B is such that the tubes 42A, 42B are only partially inside the apertures 32A, 32B and the top portion 46 of the tubes 42A, 42B are exposed to the atmosphere. Some or all of the middle portion 47 can also be exposed to the atmosphere. As provided below, even though the top portion 46 is exposed, the temperature of the biological sample in the tube 42A, 42B is able to reach a predetermined temperature (such as 65° C.) and remain at the predetermined temperature. (Also see FIG. 5 which shows multiple test tubes 42 in the apertures of the sample compartment.) The volume of the sample is very small, relative to the overall volume of the tubes 42A, 42B and thus the temperature can be maintained. A size and shape of the apertures 32A, 32B can vary and can depend on the type and size of test tubes to be used in the device 10.

The test tube/compartment design offers easy handling and operation, with an added advantage of reducing/minimizing an overall weight of the device 10. The biological sample and reagents (described below) are contained within the portion of the tubes 42A, 42B that are immersed in the compartment 26A, 26B, where the temperature remains generally uniform at 65° C. (see FIG. 9). In an example, a layer of oil encapsulates the samples, which helps in better mixing of the reagents and prevents evaporation of the samples. This is described further below.

The test tube 42A, 42B can be a single-use tube made from one or more plastics, including, but not limited to, neoprene, nylon, polypropylene, polytetrafluoroethylene, polyurethane and polyvinyl chloride. In an example, polypropylene can be used given its chemical and thermal resistance. An example polypropylene sample tube (0.5 ml) can be purchased from Eppendorf.

In both designs of sample compartment 26A, 26B, the heater 24A and 24B can be set to a predetermined temperature, such as, for example, 65° C. The heater 24A, 24B can be a solid-state thermoelectric heater and can be controlled by a temperature controller. In an example, the thermoelectric heater is from Laird Thermal Systems, Inc. The thermally conductive components (liner 38A, layer 44B) can aid in bringing the sample to a predetermined temperature during the amplification reaction. The sample compartment 26A, 26B can be thermally isolated and insulated within the interior 22 to prevent or minimize heating of the sides 14, 16, 20 that form the exterior 12 of the device 10. In an example, a thermally insulating material can be added within the interior 22 to fill a gap surrounding the compartment (26A, 26B) and the housing to enhance thermal insulation.

FIG. 5 is a perspective view of the sample compartment 26 (which represents both compartments 26A and 26B of FIGS. 3 and 4, respectively) with the tubes 42 received in the apertures 32, and FIG. 6 is a cross-sectional view of FIG. 5. For simplicity, the cap 50 and ring 52 of the tubes 42 are not included in FIGS. 5 and 6. As shown in FIG. 6, the conical bottom portion 48 of the tubes 42 can be releasably retained inside the apertures 32. As described above in reference to FIGS. 3 and 4, surfaces 54 of the apertures 32 can include a thermally conductive layer, particularly if there is open space between the surfaces 54 and the bottom portion 48 of the tubes 42.

A simulation was performed in COMSOL Multiphysics for each design of FIGS. 3 and 4 using the 'Heat Transfer' module to simulate (i) heat conduction within the compartment and (ii) natural convection of heat from the outside surfaces of the compartment to open air. The following conditions were used in the simulation: heater 24A, 24B set to 65° C.; continuity boundary condition between the compartment 26A, 26B and the surrounding air; and a 'Heat Flux' boundary condition applied to the top and side walls of the compartment 26A, 26B and tubes 42A, 42B. The heat flux boundary condition utilized a built-in convective heat transfer coefficient correlation function along with the ambient temperature (set at 25° C.) to simulate the heat flux from the walls to atmosphere (open air).

The thermal properties of aluminum provided in the COMSOL material library were used, in addition to user-defined properties for the thermally conductive material of the liner 38A and layer 44B: heat capacity at constant pressure Cp=920 J/(kg.K); density ρ=2700 kg/m³; thermal conductivity k=1.8 W/m.K); and 0.5 mL polypropylene sample tubes (Cp=1800 J/(kg.K; ρ=920 kg/m³; k=0.11-0.44 W/m.K).

FIGS. 7 and 8 show the temperature profiles of the compartment and tubes obtained under the COMSOL Multiphysics time-dependent simulations. Specifically, FIG. 7 shows the temperature distribution for the design in FIG. 4 (compartment 26 formed of metal with a thermally conductive layer 44 under the compartment 26) at time intervals of 0, 1, 5 and 30 minutes of heating; FIG. 8 shows the temperature distribution for the design in FIG. 3 (thermally conductive liner 38 covers the metal compartment 26) at time intervals of 0, 1, 5 and 30 minutes of heating.

FIG. 7 illustrates that the compartment 26 design of FIG. 4 attained the desired temperature (65° C.) within one minute of heating. By contrast, the compartment 26 design of FIG. 3 did not reach complete heating up to 65° C. even after thirty minutes of heating.

Figure 9:
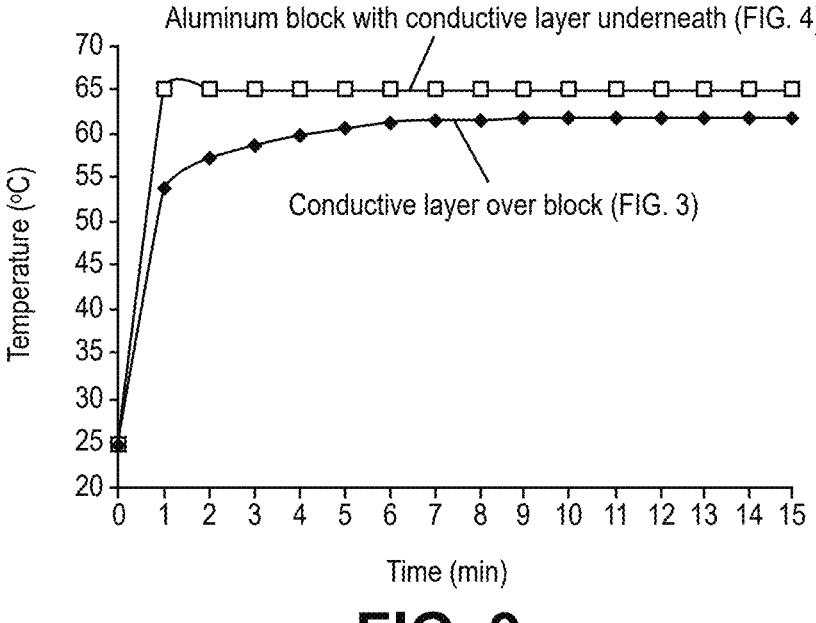
FIG. 9 is a plot of temperature as a function of heating time for the temperature profiles of FIGS. 7 and 8.

FIG. 9 illustrates the results shown in FIGS. 7 and 8 as a plot of temperature (on an upper surface of the compartment) as a function of heating time from 0 to 15 minutes. As shown in FIG. 9, the aluminum compartment of FIG. 4 reached 65° C. relatively quickly, whereas the compartment/liner of FIG. 3 plateaued at less than 65° C.

The simulated results in FIGS. 7-9 demonstrate that the compartment design in FIG. 4 is superior to the design in FIG. 3 in terms of thermal properties. Moreover, the device 10 incorporating the design of FIG. 4 rather than the design of FIG. 3 is lower in an overall weight of the device 10, which is an added advantage.

Figure 10:
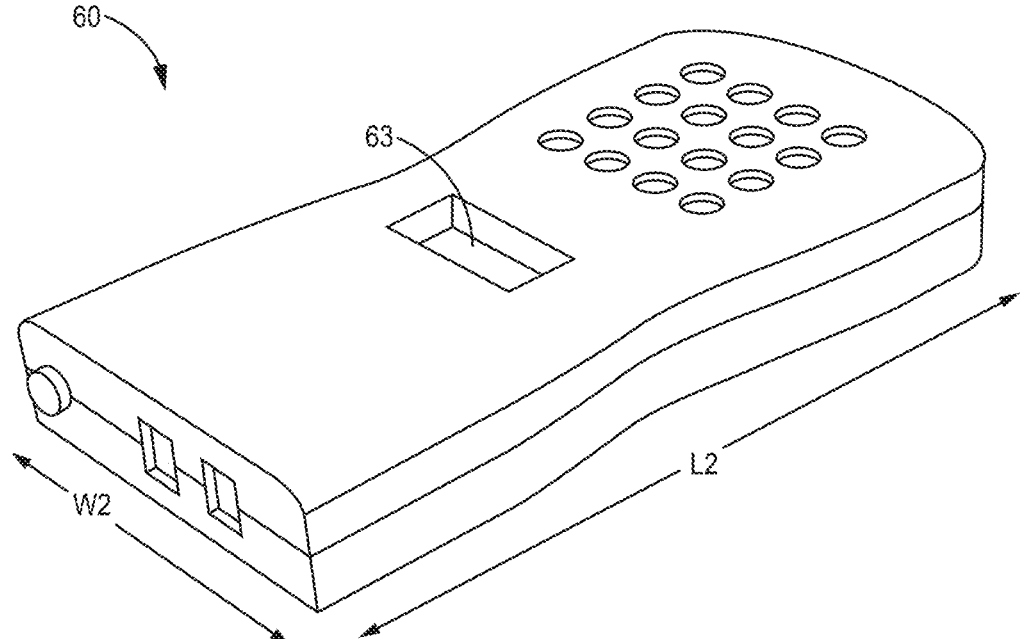
FIG. 10 is a perspective view of another example rapid detection device, according to one or more embodiments of the present disclosure.

FIG. 10 shows another example of a device 60 for the detection of one or more pathogens, including SARS-CoV-2. The device 60 is similar to the device 10 in design and function. By using one control board in the device 60 (as described below), an overall size of the device 60 is less than that of the device 10. A length L2 of the device 60 is less than the length L of the device 10. In an example, the length L2 is twenty-five percent less than the length L. In an example, the length L2 is about 150 mm and a width W2 of the device 60 is about 75 mm.

Figure 11:
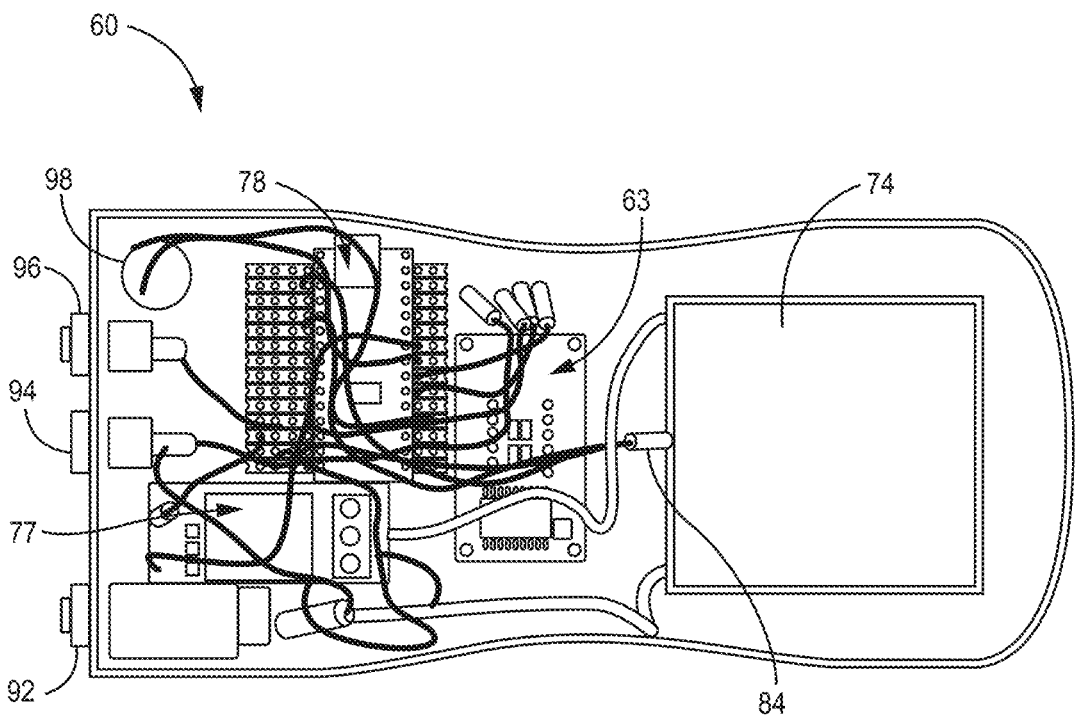
FIG. 11 is a top view of the device of FIG. 10 rotated 180 degrees and with the back cover removed from the device.

FIG. 11 shows the device 60 after a back cover has been removed from the device 60 and an interior 72 of the device 60 is visible. Rather than having two controllers (see boards 28 and 29 in FIG. 2), the device 60 can include a single controller 78 for controlling both time and temperature. As such, the device 60 can include a single display unit 63 to display both time and temperature.

In the design of the device 60, all components requiring power use 5V, so a DC regulator is not required. The device 60 can include a relay 77 for switching of the heater 24 on and off. Such separate component was not part of the design of the device 10, rather switching the heater 24 on and off was part of the temperature control unit 29.

Other components of the device 60 can be similar to the device 10, including a heater 74, a thermocouple 84 and a sample compartment (not shown) attached to the heater 74 and configured for receiving multiple test tubes. FIG. 11 shows a power connector 92, a power switch 94, a timer switch 96 and a buzzer 98.

Figure 12:
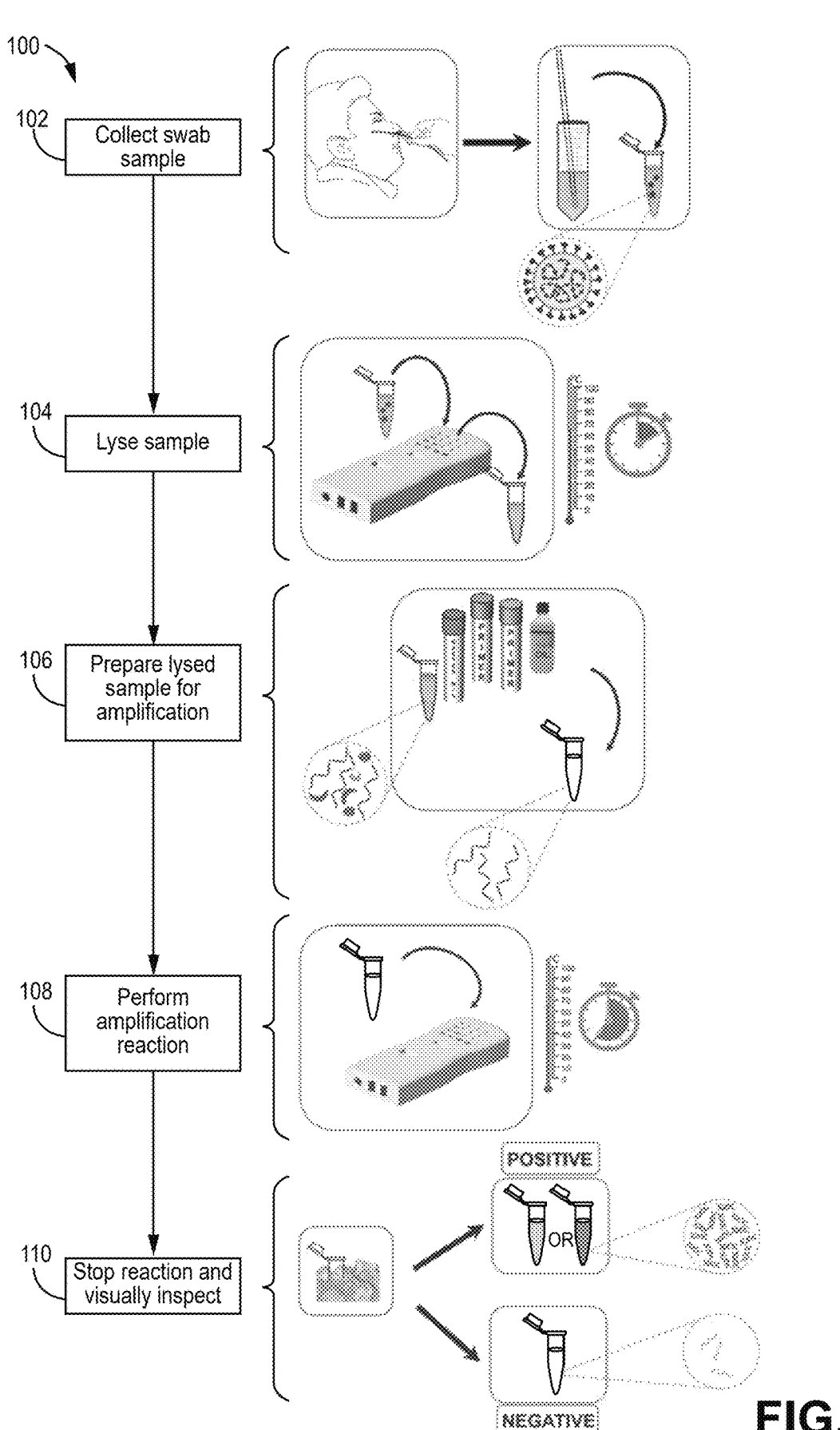
FIG. 12 is a combined process flow chart and schematic of a method of using the device of FIGS. 1 and 10 to perform reverse transcription loop-mediated isothermal amplification (RT-LAMP), according to one or more embodiments of the present disclosure.

FIG. 12 is a combined process flow chart and schematic to illustrate a method of use 100 of the device 10 for the detection of one or more pathogens. The exemplary pathogen used in the device 10 and method 100 of FIG. 12 is COVID-19.

In method 100, a first step 102 includes collecting a swab sample (a nasopharyngeal sample) and placing the sample in a test tube. In step 104, the biological sample is lysed by pre-heating the sample for a predetermined time (about 10 minutes) and at a predetermined temperature (about 65° C.). Next, the lysed sample is prepared for amplification in step 106. The lysed sample (about 2 μL) is placed into a new test tube and then mixed with one or more primers and other chemicals or enzymes. As part of the preparation, the mixture can be vortexed. The amplification reaction is then performed by heating the mixture in the tube for a predetermined time (about 35 mins) and at a predetermined temperature (about 65° C.). After the predetermined heating time, the tube can be placed on ice for a minute or less (for example, 30 seconds) to stop the amplification reaction in step 110. Once cooled, the sample in the tube is visually inspected by the naked eye or a color detection sensor. A visible color change to yellow or orange is observed for a sample having a positive result, whereas a fuchsia color represents a negative result. The fuchsia color is an indication of no amplification of the targeted genes for the one or more pathogens to be detected (i.e., N and E genes for SARS-CoV-2).

After step 110, the test tubes containing the samples can be disposed of. The device 10 can be reused for performing detection on additional biological samples (directly after or at a later time). The device 10 can be easily stored until further testing is done. Steps 102 through 110 can be repeated for each new set of biological samples.

As provided above, the process following the collection of nasopharyngeal samples until the detection of SARS-CoV-2 RNA in the device is performed in a short timeframe (for example, 45 minutes or less). The short processing time of the device is a direct consequence of elimination of the RNA extraction step. Most commercial kits require extracted pure RNA as the input for the amplification step, and as such, additional extraction steps are required prior to the amplification to perform lysis, RNA isolation, and remove inhibitory agents. The more popular and conventional RNA extraction methods involve the use of magnetic beads and/or chemical solutions to isolate the RNA from the samples. Hence, these methods not only increase the processing time but also add complexity, including in some cases additional instruments. In contrast, the device and methods of the present disclosure have the advantages of simplicity and short processing time.

Part of the preparation of the sample for amplification (step 106) can include the addition of oil to the top of the mixture in the test tubes, after the other components in step 106 have been mixed. Silicone oil can be used as a seal and to prevent evaporation of the sample in the test tube. The efficacy of silicone oil on the RT-LAMP process was investigated using two samples—one with silicone oil and the other without. Other oils can be used as an alternative or in addition to silicone oil.

FIGS. 13A and 13B show two biological samples during the amplification process—after the tubes have been heated and before placing the tubes on ice. The top and side views in FIG. 13A and FIG. 13B show that sample 56 without silicone oil had vapor deposition on the side walls and cap of the test tube, whereas sample 58 with silicone oil did not have visible condensation on the test tube. The side view of FIG. 13B shows that that there was a notable loss in volume (through evaporation) of sample 56, whereas the level of sample 58 was not affected by evaporation. Evaporation is undesirable in the amplification process, especially given the low starting volume of the samples. The results in FIGS. 13A and 13B demonstrate that the oil layer works favorable to encapsulate the biological sample and prevent evaporation. The insulating oil layer can also serve to enhance circulation of the sample mixture it covers. Consequently, a better mixing is obtained during the amplification process. In addition, a sharpness in the final colors (after amplification) of the samples with silicone oil was observed.

As provided in the examples below, a number of biological samples were tested for COVID-19 with the RT-LAMP process described herein and compared to test results obtained using the traditional PCR process. The results confirm the efficacy of the RT-LAMP process, including both sensitivity and specificity at 100% accuracy. The device is easily scalable and provides the capability to increase the number of samples tested at one time, while simultaneously offering a portable and easy to use device. Moreover, a robustness of the device allows for its use in the diagnostics of other pathogens. Such enhanced testing capabilities can provide rapid and widespread testing, both for COVID-19 and future outbreaks.

EXAMPLES

Samples were tested under both the traditional PCR process and the RT-LAMP process (using the device described herein and shown in FIGS. 1 and 2). For each process, 141 samples were tested—93 samples taken from human patients infected with COVID-19 (positive samples) and 48 negative samples from humans that tested negative under the traditional PCR test. Thus, the same biological sample was tested for COVID-19 under both PCR and RT-LAMP. The testing under RT-LAMP was completed over multiple days and using different devices.

The methods and acceptance criteria to demonstrate that an assay is valid and appropriate for its intended application have been established by the College of American Pathology (CAP) and Clinical Laboratory Improvement Amendments (CLIA). All experiments in the current work were performed in accordance with relevant guidelines and regulations and fulfill local (Health Authority Abu Dhabi-HAAD) and international (CAP) requirements for operation and accreditation purposes. COVID-19 samples were obtained from hospitals and quarantine areas in Abu Dhabi. An informed written consent form was obtained in accordance with the Declaration of Helsinki. The sample collection was approved by the local ethics committee at Abu Dhabi Health COVID-19 Research Ethics and SEHA Research Ethics Committee.

Example 1

Comparative example: The samples for the PCR process were prepared and tested using the protocol schematically shown in FIG. 14. The first step is to collect a nasopharyngeal sample and extract the RNA from the sample using an extraction kit—Promega Maxwell® RSC Viral Total Nucleic Add Purification Kit from Promega. Next, the extracted RNA is aliquoted and RT-qPCR is performed using NeoPlex™ COVID-19 Detection Kit for 40 cycles on Bio-Rad CFX96 Touch Real-TIM PCR Detection System from Bio-Rad Laboratories, Inc.

The PCR reaction is prepared by adding 5 µl of the COVID-19 PPM, one-step Master Mix, DW (RNase-free Water), and 5 µl of the extracted RNA sample for a total of 20 µl. Then the prepared mixture is vortexed and briefly centrifuged using a microfuge. Finally, 15 µl aliquots of the PCR Master Mix is placed into 0.2 ml PCR tubes.

Figures 15A, 15B:
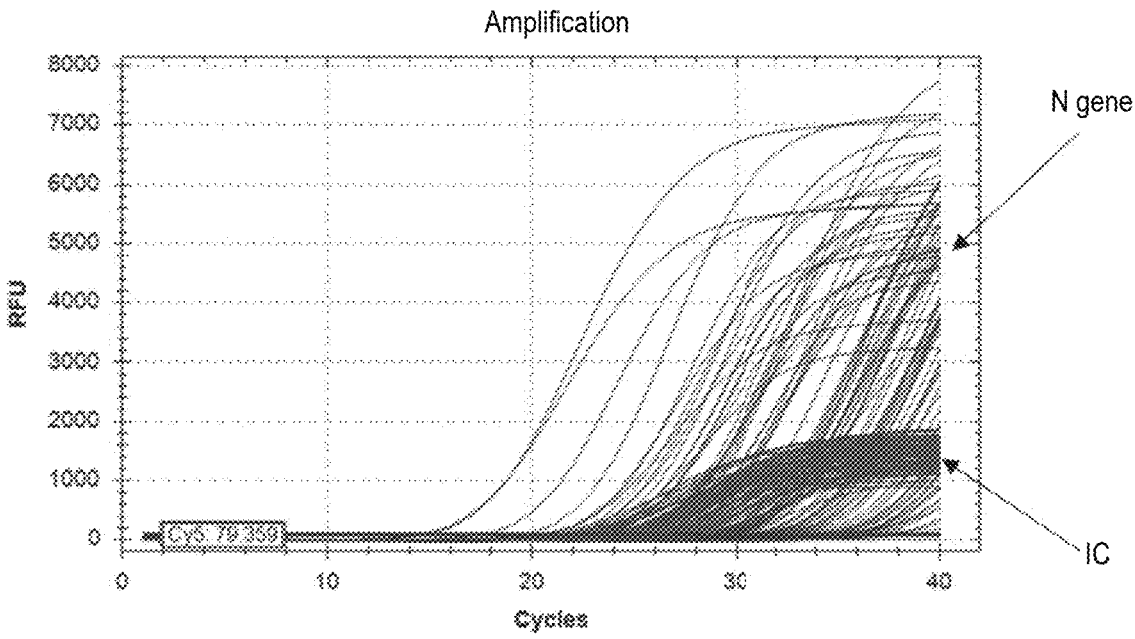
FIGS. 15A and 15B are amplification curves of positive and negative COVID-19 samples tested under the process of FIG. 14.

FIGS. 15A and 15B show the amplification curves of the samples tested under the PCR process. FIG. 15A presents the positive samples and FIG. 15B presents the negative samples. The group of curves labeled "N gene" indicate that there is an amplification of the N gene of SARS-CoV-2 in the patient samples; the group of curves labeled "IC" are indicative of the Internal Control (IC). The "N gene" curves in FIG. 15A represent a successful amplification with each cycle crossing the fluorescence threshold value (cycle threshold $C_t$) at a different value in the range of 0-40 cycles. The cycle threshold $C_t$ represents the viral load in a sample. A lower $C_t$ correlates to a higher amount of nucleic acid in the sample, and vice versa. In FIG. 15A, all the internal control samples are also amplified, indicating that the extraction step and PCR amplifications are valid for all the positive samples. As shown in FIG. 15B, only the positive control sample showed amplification.

Out of the 93 positive samples, the RT-qPCR assay detected 90 samples as positive, whereas three samples were detected as negative. Thus, the total number of negative samples amounted to 51 under the RT-PCR technique.

Example 2

Figure 16:
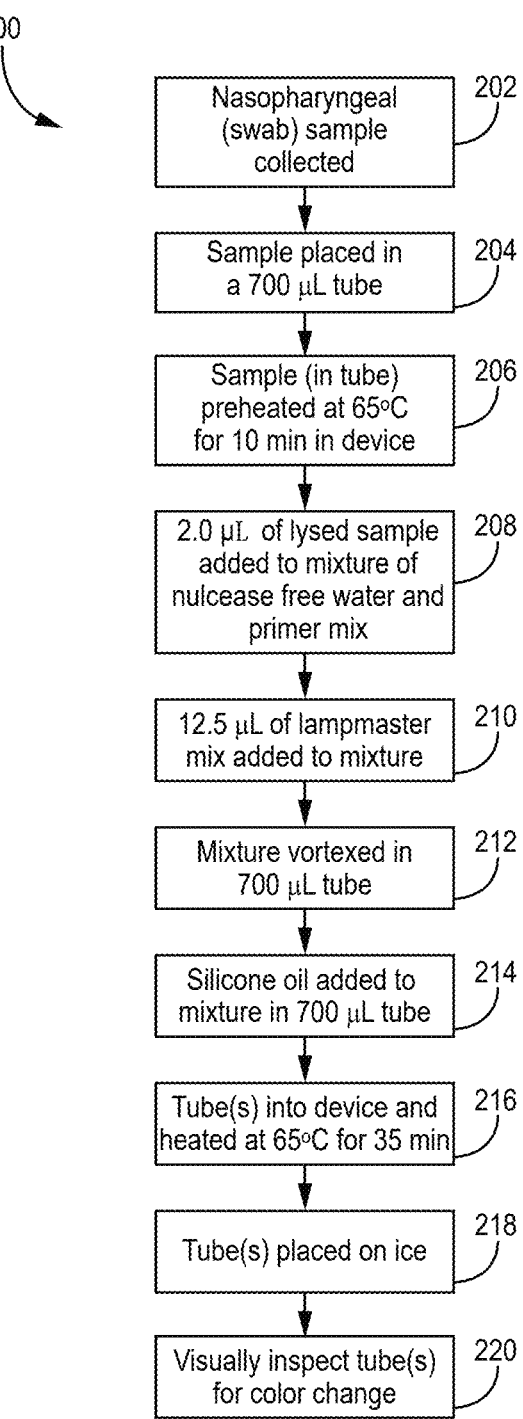
FIG. 16 is a process flow chart of an experimental protocol for using the device of FIG. 1 or 10 to perform RT-LAMP, according to one or more embodiments of the present disclosure.

Protocol: The experimental protocol used for the RT-LAMP process is shown in FIG. 16. A protocol 200 includes use of the portable, reusable device 10 of FIGS. 1 and 2 to detect SARS-Co-V-2; the protocol 200 is also schematically represented in FIG. 12.

The protocol 200 also begins in step 202 with collecting a nasopharyngeal sample. In step 204, about 30 µL of the nasopharyngeal swab sample is placed in a 700 µL Eppendorf tube. The tube is placed into an aperture formed in the sample compartment of the device and preheated at 65° C. for 10 minutes (step 206). Such preheating step lyses the cells and viral capsid in the sample to release the organelles, including the viral RNA.

In step 208, 2 µL of the lysed sample is added to a 10 µL mixture containing 7.5 µL of nuclease-free water and 2.5 µL of a target specific primer mix to detect the target regions from two genes—nucleocapsid (N) and envelope (E)—from the SARS-CoV-2 viral genome. In step 210, 12.5 µL of WarmStart Colorimetric LAMP 2X Master Mix from New England BioLabs Inc is added to the sample mixture from step 208. The mixture from step 210 is vortexed in a 700 μL Eppendorf tube (step 212) to mix all the reagents. In step 214, 5 μL of silicone oil is added to the mixture to encapsulate the mixture at the top of the tube and prevent evaporation.

Next the tube containing the prepared sample is placed in the aperture of the device and heated at 65° C. for 35 minutes (step 216) to start the amplification reaction. The time and temperature in steps 206 and 216 can be monitored by the device. After 35 minutes, the tube is removed from the device and placed on ice for 30 seconds in step 218 to stop the reaction. The sample in the tube is visually inspected by the naked eye (step 220). A visible color change to yellow or orange represents a positive result, whereas a fuchsia color represents a negative result (i.e., no amplification of the targeted genes N and E for SARS-CoV-2).

The protocol 200 is repeated for each sample and multiple samples were tested at the same time in the device 10.

Figure 17:
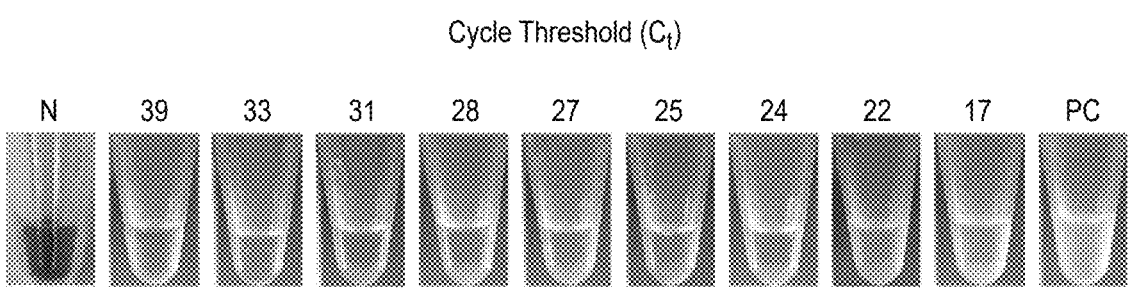
FIG. 17 shows photographic images of various samples after performing the protocol of FIG. 12 or 16 to test for COVID-19 to illustrate color change, according to one or more embodiments of the present disclosure.

Results: The results of the RT-LAMP assays are shown in FIG. 17. The photographs show the pink to yellow/orange color change in the positive samples at the end of 35 minutes of incubation, in comparison to a fuchsia color obtained with all the negative samples. FIG. 17 also shows the different RT-qPCR-derived cycle threshold (C_t) values for that same sample for use in evaluating the LAMP process.

As evidenced by FIG. 17, it was possible to detect a color change in the LAMP process for a sample that yielded a cycle threshold (C_t) as high as 39. The incubation time in the protocol described herein is optimized to eliminate a color change in the negative samples and negative control towards a yellowish color, which can be caused by spurious amplification products. All the samples were photographed under the same conditions.

The dependence of the degree of pink-to-yellow color change on the cycle threshold (C_t) was quantified by computing the color difference between the positive samples and negative control, normalized to the difference between the Positive Control and Negative Control using the R, G, B linear dimensions defining the color space. The following equation was used:

$$RGB \text{ distance ratio} = \frac{\sqrt{(R_s - R_{NC})^2 + (G_s - G_{NC})^2 + (B_s - B_{NC})^2}}{\sqrt{(R_{PC} - R_{NC})^2 + (G_{PC} - G_{NC})^2 + (B_{PC} - B_{NC})^2}}$$

where the subscripts S, NC and PC are sample, Negative Control, and Positive Control, respectively.

Figure 18:
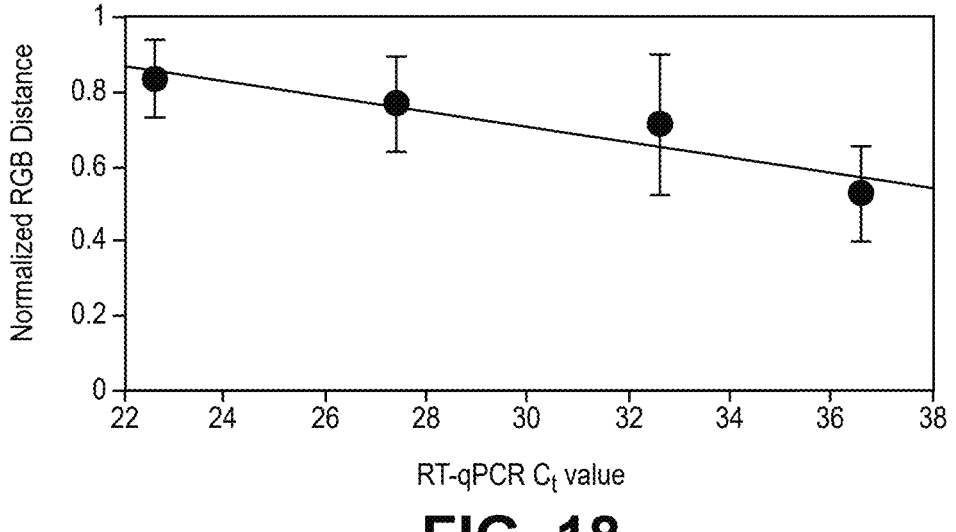
FIG. 18 is a plot of the normalized RGB distance for color change under RT-LAMP as a function of a cycle threshold value under RT-PCR.

The RT-qPCR positive samples were categorized by their cycle threshold (C_t) values into four groups (C_t equal to 0-25, 25-30, 30-35 and 35-40—see Table 2 below). FIG. 18 shows the average normalized RGB distance for each category. The standard deviation error bars shown in FIG. 18 represent the distribution of the normalized RGB distance of the samples categorized in each of the four groups. The data demonstrates a correlation between the color difference and the RT-qPCR derived cycle threshold (C_t) value, with the color difference being higher for lower C_t values.

TABLE 2

| Positive and negative samples from RT-LAMP in groups on C_t from RT-qPCR | | | | | |
| --- | --- | --- | --- | --- | --- |
| | | | RT-LAMP | | |
| | | C_t | Positive | Negative | Sum |
| RT-qPCR | Positive | 0-25 | 15 | 0 | 15 |
| | | 25-30 | 18 | 0 | 18 |
| | | 30-35 | 34 | 0 | 34 |
| | | 35-40 | 23 | 0 | 23 |
| | Negative | Negative | 3 | 48 | 51 |
| | | Sum | 93 | 48 | 141 |

The RT-LAMP device and process successfully detected all 93 positive samples and all 48 negative samples. The overall clinical specificity (calculated using the ratio of the number of true negatives over the number of true negatives plus number of the false positives) was 100%. Moreover, the sensitivity (the ratio of the number of true positives over the number of true positives plus the number of false negatives) was also 100%.

Thus, the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto.

Various examples have been described. These and other examples are within the scope of the following claims.

What is claimed is:

1. A portable, reusable device for detection of one or more pathogens using a reverse transcription loop-mediated isothermal amplification (RT-LAMP) process, the device comprising:

a sample compartment contained within an interior of the device and having multiple apertures formed in a top surface, the multiple apertures aligned with exterior apertures formed on an exterior of the device, each of the apertures of the multiple apertures configured to releasably receive a bottom portion of a test tube containing a biological sample, and a top portion of the test tube is exposed to atmosphere when the bottom portion is received in the aperture;

a heating source to increase a temperature of the sample compartment and the one or more biological samples to a predetermined temperature when the test tube is received in the aperture;

and a power source for providing electrical power to the heating source;

a temperature sensor capable of detecting the temperature of the one or more biological samples; and a controller connected to the heating source and the temperature sensor programmed to control an output of the heating source to maintain the temperatures of the sample compartment and the one or more biological samples after the one or more biological samples reach temperatures suitable for lysis and temperatures suitable for RT-LAMP, wherein the device has size and weight suitable to be handheld.

2. The device of claim 1, further comprising:

a thermally conductive material for use with the heating source to maintain the temperatures of the sample compartment and the one or more biological samples.

3. The device of claim 2, wherein the thermally conductive material is located on a surface of each of the multiple apertures for proximity to the bottom portion of the one or more test tubes.

4. The device of claim 2, wherein the thermally conductive material comprises an elastomer.

5. The device of claim 1, wherein the multiple apertures comprise sixteen or more apertures.

6. The device of claim 1, wherein the heating source is a solid-state thermoelectric heater.

7. The device of claim 1, wherein the power source is a low voltage adapter.

8. The device of claim 1, further comprising:

a housing that forms an exterior of the device, wherein the sample compartment, the heating source, the temperature sensor, and the controller are contained within the interior of the device.

9. The device of claim 8, further comprising a thermally conductive material located between an underside of the housing and the heating source.

10. The device of claim 8, wherein the housing that forms the exterior of the device is formed via three-dimensional (3D) printing.

11. A portable, reusable device for detection of one or more pathogens using a reverse transcription loop-mediated isothermal amplification (RT-LAMP) process, the device consisting essentially of:

a sample compartment contained within an interior of the device and having multiple apertures formed in a top surface, the multiple apertures aligned with exterior apertures formed on an exterior of the device, each of the apertures of the multiple apertures configured to releasably receive a bottom portion of a test tube containing a biological sample, and a top portion of the test tube is exposed to atmosphere when the bottom portion is received in the aperture;

a heating source to increase a temperature of the sample compartment and the one or more biological samples to a predetermined temperature when the test tube is received in the aperture;

one or more power sources for providing electrical power to the heating source;

a temperature sensor capable of detecting the temperature of the one or more biological samples; and a controller connected to the heating source and the temperature sensor programmed to control an output of the heating source to maintain the temperatures of the one or more biological samples after they reach temperatures suitable for lysis and temperatures suitable for RT-LAMP.

12. The device of claim 11, wherein the multiple apertures comprise sixteen or more apertures.

13. The device of claim 11, wherein the heating source is a solid-state thermoelectric heater.

14. The device of claim 11, wherein the power source is a low voltage adapter.

* * * * *